United States Patent [19]

Sutter

[11] Patent Number: 5,549,704

[45] Date of Patent: Aug. 27, 1996

[54] UNIVERSAL JOINT PROSTHESIS

[76] Inventor: Franz Sutter, Bennwilerstrasse 42, 4435 Niederdorf, Switzerland

[21] Appl. No.: 413,180

[22] Filed: Mar. 30, 1995

[30] Foreign Application Priority Data

Sep. 8, 1994 [CH] Switzerland ............................. 2745/94

[51] Int. Cl.$^6$ ...................................................... A61F 2/32
[52] U.S. Cl. ................................................. 623/23; 623/18
[58] Field of Search ................................. 623/16, 18, 19, 623/20, 22, 23; 606/65, 66, 67

[56] References Cited

U.S. PATENT DOCUMENTS

| | | | |
|---|---|---|---|
| 4,752,296 | 6/1988 | Buechel et al. | 623/23 |
| 4,865,603 | 9/1989 | Noiles | 623/16 |
| 5,002,579 | 3/1991 | Copf et al. | 623/16 |
| 5,080,679 | 1/1992 | Pratt et al. | 623/23 |
| 5,108,435 | 4/1952 | Gustavson et al. | 623/16 |
| 5,236,459 | 8/1993 | Koch et al. | 623/16 |

FOREIGN PATENT DOCUMENTS

| | | | |
|---|---|---|---|
| 0098224 | 1/1984 | European Pat. Off. | 623/23 |
| 2318459 | 10/1974 | Germany | 623/22 |
| 2819178 | 11/1979 | Germany | 623/23 |

Primary Examiner—David Isabella
Attorney, Agent, or Firm—McGlew and Tuttle, P.C.

[57] ABSTRACT

The universal joint prosthesis has a cap which has an outer shell, an inner shell, a calotte-shaped, smooth outer surface formed by the outer shell and an inner surface formed by the inner shell and having projections distributed along the circumference. At least some projections have undercuts and/or are provided with through holes. The outer material forming the outer shell has, with the same surface characteristics, a smaller coefficient of friction than the inner material forming the inner shell. On the other hand, the inner material permits a firmer bond with a bone than the outer material. The universal joint prosthesis also has perforated sleeves projecting from the cap. The universal joint prothesis can usually be attached firmly to a bone without a binder, the undercuts and/or holes helping to provide a permanent connection between the cap and the bone.

19 Claims, 5 Drawing Sheets

UNIVERSAL JOINT PROSTHESIS

FIELD OF THE INVENTION

The invention relates to a universal joint prosthesis or—more specifically to—a universal joint endoprosthesis intended for attachment to a bone.

The universal joint prosthesis is intended in particular for attachment to a femur of a human or possibly of an animal, for example of a dog, for forming the artificial head of a hip joint. The head may be supported in a likewise artificial socket or in the natural socket consisting of bone material.

BACKGROUND OF THE INVENTION

Known metallic universal joint prostheses for hip joints have a complete, spherical head and a bent or curved stem or shaft connected rigidly thereto, wherein the head and the stem or shaft have essentially full cross-sections, i.e. are free of holes. In order to attach such a prosthesis to a bone, i.e. the femur, the natural head and a part of the neck of the femur are cut off and a hole is drilled in the shaft of the femur so that a great deal of bone material has to be removed and many blood vessels are destroyed. In addition, the bent or curved metallic prosthesis stem or shaft which is usually cemented into the femur shaft has a much greater bending strength than a natural femur. This has the disadvantage that, under loads, regions of the femur which are adjacent to the stem or shaft and possibly also other parts of the body frequently experience much stronger and/or weaker localized stresses than in the case of corresponding loads on a completely natural femur, and that consequently the long-term stability of the connection between the prosthesis and the femur may be impaired.

Universal joint prostheses disclosed in U.S. Pat. No. 4,328,593 and U.S. Pat. No. 4,332,036 have a cap and a stem which consists of a cylindrical sleeve having a perforated jacket. The cap has a calotte-shaped, smooth outer surface and an inner surface having projections and recesses distributed along the circumference. These known prostheses consist, for example, of titanium, the inner surface of the cap and the sleeve having a thin porous titanium coating applied by a plasma spraying method.

Compared with the prostheses having a solid head and a solid, bent or curved stem or shaft cemented in the bone, these prostheses having a cap and a sleeve of titanium have the advantages that only relatively little bone material must be removed for attaching the prosthesis. Furthermore, the bone material can readily grow to the inner surface of the cap and also unite with the perforated sleeve, so that the prostheses disclosed in the cited U.S. Pat. Nos. 4,328,593 and 4,332,036 are connected relatively firmly to bones without cement. In the case of extremely severe and/or quickly changing loads, however, there is in fact a certain danger that the connection between the inner surface of the cap and the bone will experience localized loosening.

Since the sleeve of the prostheses disclosed in the cited U.S. Pat. Nos. 4,328,593 and 4,332,036 has a relatively large diameter, it is furthermore difficult in certain cases to cut the annular hole which serves for receiving the sleeve into the bone without damaging blood vessels or causing other injuries during the operation. Another certain disadvantage of these known prostheses is that the calotte-shaped outer surface of a titanium cap—even when it is polished smooth—gives rise to relatively great fiction in the case of movements in an artificial or natural socket and causes relatively pronounced wear of the socket and/or is itself worn away.

SUMMARY OF THE INVENTION

It is an object of the invention to provide a universal joint prosthesis which makes it possible to avoid the disadvantages of the known prostheses. Starting in particular from the universal joint prostheses disclosed in U.S. Pat. Nos. 4,328,593 and 4,332,036, it is desirable to permit a firm and permanent connection between the inner surface of the cap and the bone even in the case of extremely severe loads and/or loads which quickly change their direction.

The foregoing and other objects are attained in accordance with the invention by a universal joint prosthesis having a cap which has a calotte-shaped or (hollow) cup shaped outer surface and an inner surface intended for attachment to a bone, in particular a femur, and defines a cap axis, wherein said inner surface is provided with a number of projections distributed along its circumference, wherein at least some of said projections are at least one of undercut and comprising a hole with a hole axis which makes an angle with a normal to a section of an osculating surface which closely fits the projections and is rotationally symmetrical with respect to said cap axis, said section being located adjacent to the relevant hole.

If projections having a hole are present, the angle made by the hole axis with the stated normal is preferably approximately a right angle.

In a surgical operation intended for attaching a universal joint prosthesis according to the invention to a bone—for example to a human or animal femur—a bone stump can be formed by cutting away a part of the natural head and the cap can be fitted onto said stump. The bone stump is preferably shaped and dimensioned in such a way that the bone material engages between the projections or in the indentations as soon as the cap is fitted. The cap then fits relatively firmly on the bone stump immediately after the operation, even without attachment by means of bone cement or another binder. During a healing process following the operation, the bone can grow so that it at least essentially completely fills the indentations and/or other cavities present within the cap and in particular also the undercuts and/or holes. The inner surface of the cap will therefore be thoroughly anchored to or in the bone and more or less covered therewith after healing of the bone at the latest. This prevents the bone and the inner surface of the cap from becoming detached from one another even when the prosthesis is subjected to strong and/or rapidly changing forces or force components more or less transverse to the cap axis, as may occur, for example, when running quickly up or down a staircase, during jumps or the like. The undercuts and/or holes therefore considerably help to achieve a firm and permanent connection between the prosthesis and the bone.

The outer surface of the cap and the cap edge are preferably rotationally symmetrical with respect to the cap axis. Furthermore, the inner surface preferably has a part which is cylindrical except for the projections and/or indentations and defines a cylindrical osculating surface closely fitting its projections and coaxial with the cap axis or a cylindrical section of an osculating surface. Instead of a cylindrical osculating surface or an addition thereto, the inner surface of the cap may define a slightly conical osculating surface widening toward the cap edge.

The prosthesis may have at least one stem which has an end rigidly connected to the cap, is present partially in the inner space enclosed in cross-section by the inner surface of the cap and projects from the cap. The one or more stems preferably consists of a sleeve, preferably has a straight stem or sleeve axis parallel to the cap axis and is preferably at least essentially parallel to said stem or sleeve axis. The one or more sleeves is preferably open at its end projecting from the cap and has a perforated jacket. The axial dimension (i.e. parallel to the cap axis) of the section, present outside the cap, of the one or more stems preferably consisting of a sleeve is preferably at least 10% and advantageously at most 100% of the maximum external diameter of the cap and of the sphere diameter of the osculating and/or spherical envelope surface defined by the outer surface of the cap.

If the prosthesis is used for forming the head of a human femur and, apart from the surface of the head, said femur is still in relatively good condition, the axial dimension of the stated section of the stem is preferably at most 60% and, for example, 20% to 80% of the stated sphere diameter, so that the one or more stem ends in the neck of the bone and does not project into the shaft of the bone. If, on the other hand, the bone is greatly weakened in the region of the head and neck—for example as a result of osteoporosis—it may be advantageous to make the one or more stems sufficiently long so that it projects into the shaft of the bone. The axial dimension of the section, present outside the cap, of the one or more stems may then be, for example, 30% to 100% or 50% to 100% of the stated sphere diameter.

According to another object of the invention, there is provided a universal joint prosthesis having a cap which has a calotte-shaped or cup shaped outer surface and an inner surface intended for attachment to a bone, in particular a femur, and having at least one of projections and indentations distributed along its circumference, and having at least two stems intended for attachment in the bone, each of which has an end rigidly connected to the cap and projects out of the cap through an inner cap space enclosed by the inner surface of the cap, wherein the stems have straight axes parallel to one another.

In a particularly advantageous embodiment of the prosthesis, the latter has, for example three stems or sleeves with straight stem or sleeve axes parallel to one another and to the cap axis. These stems or sleeves may then, for example, be distributed uniformly or nonuniformly around the cap axis. The individual stems or sleeves may have relatively small diameters which are preferably at most 30% and, for example, at most or about 25% of the (maximum) diameter of the stated cylindrical or possibly slightly conical osculating surface closely fitting projections of the inner surface. If a plurality of stems or sleeves are present, they can, in spite of relatively small diameters, effect good anchoring of the prosthesis and in particular good prevention of rotation of said prosthesis about the cap axis. The relatively small diameters of the stems or sleeves have the advantage that the holes which serve for receiving the stems or sleeves can be drilled in the bones without destroying many blood vessels.

When a universal joint prosthesis according to the invention is attached to a bone, a large part of the natural bone can be retained, which is very advantageous.

At least the major part of that inner surface of the cap which is adjacent to a bone in the case of implanted prostheses, preferably the entire inner surface of the cap, and the one or more stems which may be present and consist, for example, of a sleeve are preferably formed from a material which is very biocompatible and can form a firm bond with the bone.

According to another object of the invention, a universal joint prosthesis is provided, having a cap which has a calotte-shaped or cup shaped outer surface and an inner surface intended for attachment to a bone, in particular a femur, wherein the cap has an outer material forming its outer surface and an inner material forming at least the major part of its inner surface, the outer material differing from the inner material in at least one chemical component.

The outer material then consists of a chemical substance or of a mixture which differs from the inner material. The one or more preferably present stems can then likewise consist of the inner material.

For the sliding friction which takes place during movements and for the static friction, the outer material may then have coefficients of friction which are smaller than those of the inner material with the same surface characteristics and under otherwise identical conditions. Accordingly, during sliding movements of the universal joint prosthesis in an artificial or natural socket, the outer material—once again with identical surface characteristics and under otherwise identical conditions—can cause less abrasion of said socket than an outer surface consisting of the inner material. Furthermore, the outer material may have higher abrasion resistance than the inner material with identical surface characteristics and under otherwise identical conditions, so that the universal joint prosthesis also experiences only little wear even on its outer surface.

On the other hand, when the inner material is in direct contact with the bone, the inner material permits a better, stronger and more permanent bond to the bone than the outer material with the same surface characteristics.

The inner material preferably consists of a metallic material, for example at least essentially of pure titanium or of a titanium alloy or possibly of tantalum or zirconium. Preferably, at least the cap region forming the major part of the inner surface is rough and porous. The cap may have, for example, a compact, pore-free inner shell which consists of one of the stated inner materials and on whose inner surface a thin, porous layer forming at least the major part of the inner surface of the cap is applied by a plasma spray process, which layer for the most part consists of titanium but may also contain a small amount of titanium oxide nitride or titanium dioxide formed during spray application and also a small amount of carbon and of gases dissolved in the metal.

When titanium comes into contact with air, water or an electrolyte, oxide forms spontaneously on its surface. This oxide forms a compact film which protects the metal underneath from corrosion. The oxide film protects the metal in particular from the liquids present in a human or animal body, so that the titanium in a body is virtually insoluble, in particular releases no ions and has very high biocompatibility. In addition, titanium—in particular with a rough, porous surface—enables the bone material to grow on the inner surface of the cap.

The outer material is preferably metallic and may consist, for example, of an alloy which has cobalt as the main component. The alloy may consist, for example, of the following components: about 30% by weight of chromium, 5 to 7% by weight of molybdenum, 1 to 2% by weight of nickel, about 1% by weight of iron, about 1% by weight of silicon, about 1% by weight of manganese and about or at most 0.75% by weight of carbon, the remainder being cobalt. In addition to the main component cobalt, the alloy may also contain chromium, nickel, molybdenum and tungsten, possibly iron and possibly further components. The outer material may also consist of ceramic.

If the outer surface of a cap is polished smooth and if joint fluid or a more or less similar fluid—such as a physiological saline solution—is present between said cap and an opposite surface formed by an artificial or possibly natural socket, an outer surface formed from pure titanium gives a coefficient of friction in the range from 0.43 to 0.53 for the sliding friction. If, on the other hand, the outer material forming the outer surface consists of the cobalt alloy stated first further above, a coefficient of sliding friction which is smaller than that of titanium and is about 0.08 to 0.32 results in the case of an outer surface polished smooth under otherwise identical or at least similar conditions.

The cap may have, for example, an outer shell consisting of the outer material and an inner shell consisting of the inner material. The two shells may be produced separately and then rigidly connected to one another, for example by a press-fit and/or weld connection. Instead, an inner material may be sintered onto a shell consisting of the outer material and then forms the inner surface of the cap.

The prosthesis according to the invention can be attached to a bone without bone cement and without another binder. However, the inner surface of the cap and/or at least one preferably present stem may be connected locally by bone cement or another binder to the bone, for example in the case of diseases of the bone or in other special cases. However, the inner surface of the cap should have at least one section which possesses projections and/or indentations and remains free of binder and can come into direct contact with the bone. For example, the inner surface of the cap can be provided with at least one circular groove surrounding the cap axis. The cap can then be bound to the bone at this or each groove by means of a binder, such as bone cement.

BRIEF DESCRIPTION OF THE DRAWINGS

The subject of the invention is illustrated in more detail below with reference to embodiments shown in the drawings. In the drawings.

DESCRIPTION OF THE PREFERRED EMBODIMENTS

Figure 1:
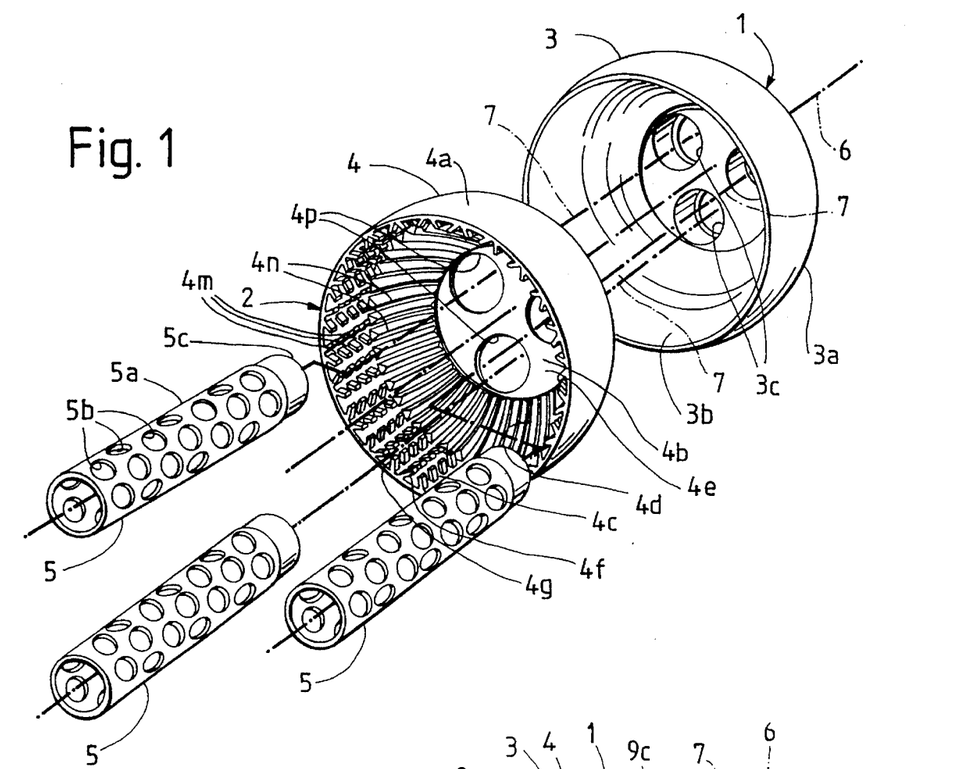
FIG. 1 is an exploded view of a universal joint prosthesis having a cap and three sleeves, the inner surface of the cap having a section with tab-like, inclined projections.
Figure 2:
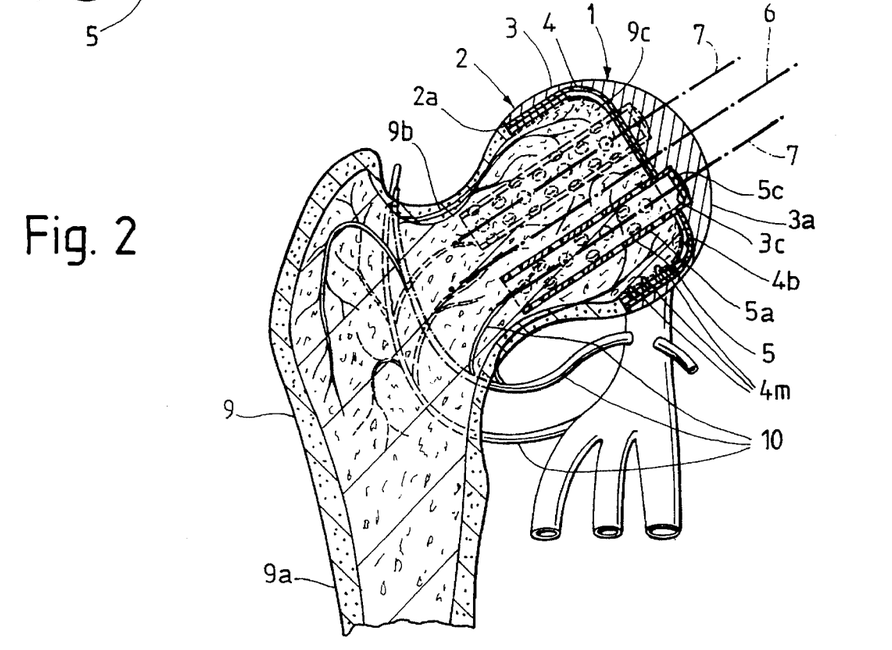
FIG. 2 shows a section through the prosthesis attached to a bone and composed of the parts shown in FIG. 1.
Figure 3:
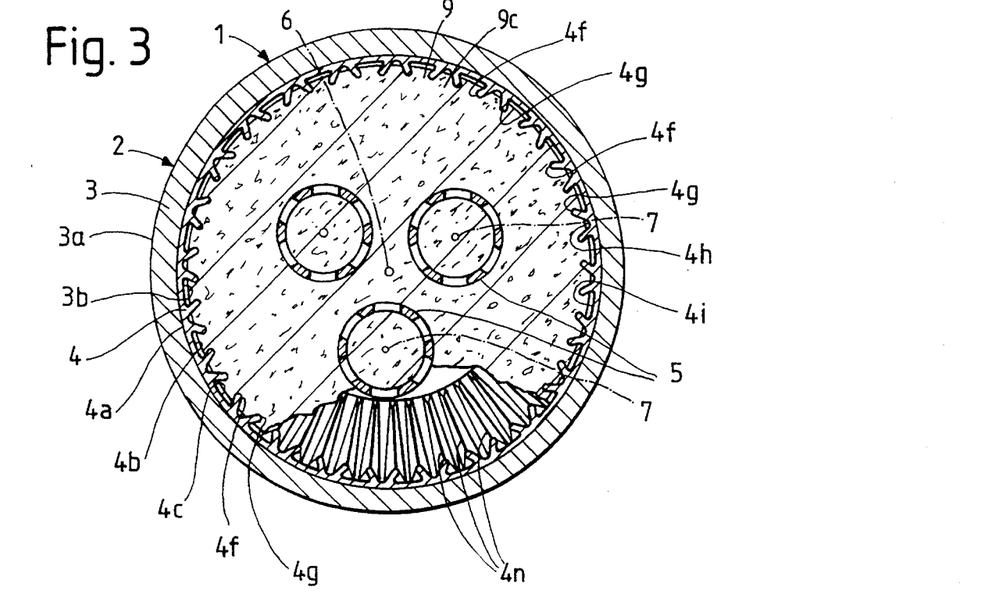
FIG. 3 is a cross-section through the bone and the prosthesis attached thereto on a larger scale than FIG. 2 and in the condition immediately after the operation.
Figure 4:
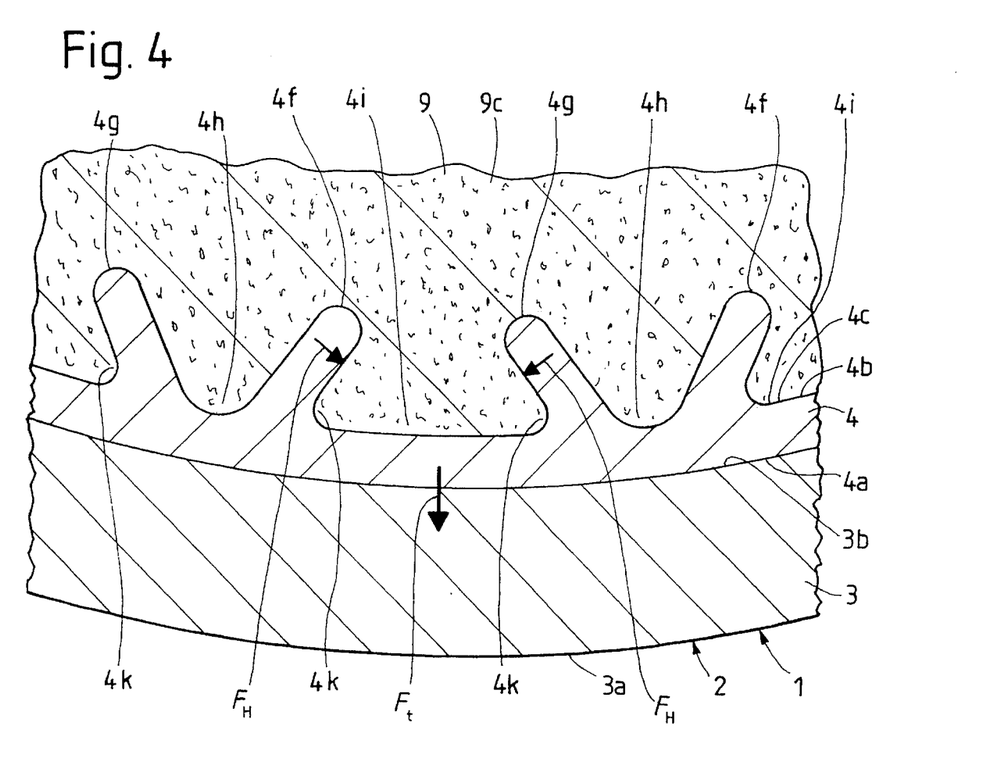
FIG. 4 is a section of the cap of the prosthesis on an even larger scale and after intergrowth of the bone.

The universal joint prosthesis 1 shown in FIGS. 1 to 3 and partly also in FIG. 4 has a cap 2. The cap 2 consists of an outer shell 3 and an inner shell 4 rigidly connected thereto. The prosthesis 1 furthermore has three stems which are rigidly connected to the cap 2 and each of which consists of a sleeve 5. The cap 2 has or defines a straight cap axis 6. Each stem consisting of a sleeve 5 has or defines a straight stem or sleeve axis 7 parallel to the cap axis 6.

The outer shell 3 of the cap 2 has a smooth outer surface 3a which also forms the outer surface of the entire cap. The outer surface 3a is calotte-shaped or cup shaped and in fact forms a spherical calotte or cup which is slightly larger than a hemisphere. The likewise smooth inner surface 3b of the outer shell 3 has a cylindrical section which is adjacent to the edge of the outer shell and is cohesive, via a transition section curved in axial section, with a flat top section at right angles to the cap axis 6. Said top section is provided with three blind holes 3c which consist of bores and have, at their base, an annular or circular contact surface at right angles to their axis.

The inner shell 4 has a smooth outer surface 4a which is complementary to the inner surface 3b of the outer shell 3 and, when the prosthesis is assembled, rests against the inner surface 3b. The inner surface 4b of the inner shell 4 also forms at least the major part of the inner surface of the entire cap and has three sections, namely a jacket section 4c adjacent to the edge of the inner shell, a transition section 4d and a top section 4e. The jacket section 4c is in general cylindrical. The transition section 4d is curved in an axial section passing through the cap axis 6 and connects the jacket section 4c continuously with the flat top section 4e at right angles to the cap axis.

The jacket section 4c is provided with a number of inward-pointing projections 4f and 4g, which are particularly clearly evident in FIGS. 3 and 4. The projections 4f and 4g are distributed around the cap axis 6, a projection 4f and a projection 4g alternating with one another along the circumference of the cap 2. Each projection 4f, 4g is tab-shaped and has two flat lateral surfaces which are parallel to one another and to the cap axis 6 and are connected continuously to one another at the free end of the projection by a curved free end transition surface.

The projections 4f and 4g adjacent to one another along the cap circumference are, in cross-section, inclined inward on different sides of planes between them and through the cap axis 6. Accordingly, the projections 4f and 4g following in succession along the circumference are inclined toward the inside—i.e. in the direction of their free ends—alternately away from one another in pairs and toward one another in pairs. An indentation 4h having an approximately V-shaped cross-section is present between each pair of projections 4f and 4g inclined away from one another in an inward direction.

The base of each indentation 4h is formed by a base transition surface which is curved in cross-section and continuously connects to one another the lateral surfaces of the projections 4f, 4g, which surfaces bound the identation 4h.

An indentation 4i which is approximately acute angled dado profiled or swallowtail-shaped in cross-section and whose regions adjacent to the projections form undercuts 4k is present between each pair of projections inclined toward one another in an inward direction. The lateral surfaces of the projections 4f, 4g, which surfaces bound an indentation 4i, are connected by curved base transition surfaces continuously to a section of the cylindrical part of the inner surface 4b. The projections 4f and 4g are also distributed in the axial direction over the jacket section 4c of the inner surface 4b. Straight rows of projections 4f parallel to the cap axis 6 and straight rows of projections 4g parallel to the cap axis are present. The projections 4f or 4g following in succession along such a row are separated from one another by identations 4m. The indentations 4h, 4i, 4m are formed by sections of intersecting, axial and annular grooves.

The transition section 4d of the inner surface 4b is provided with projections 4n, each of which consists of a rib. These ribs extend along planes passing through the cap axis 6. In cross-section, the rib-like projections 4n may have, for example, approximately the shape of an equilateral triangle or of a continuously curved waveform. The indentations which are not shown and are present between the adjacent, rib-like projections 4n have no undercuts but could also have undercuts, at least in part.

The height of the projections 4n decreases toward the top section 4e, so that the projections 4n virtually taper off completely at the edge of the top section. In addition, each rib-like projection 4n may, at its summit and at one of its flanks, be approximately aligned with one of the straight rows of projections 4f or 4g.

The top section 4e of the inner shell 4 has three through holes 4p. Each of these is aligned with one of the blind holes 3c. Each sleeve 5 has an essentially cylindrical jacket 5a, fits with its first end tightly in a pair of holes 3c, 4p aligned with one another and rests on the contact surface present at the base of the blind hole 3c. Each sleeve 5 projects through the inner space of the cap 2, which space is surrounded in cross-section by the inner surface 4b, and out of said inner space. The jacket 5a of each sleeve 5 is penetrated by holes 5b, namely bores, which are distributed uniformly over the circumference of the jacket 5a and over the axial dimension of its part present outside the holes 3c, 4p and form perforations. Each sleeve 5 is terminated at its first end inserted in a blind hole 3c by an end wall 5c whose inner surface may also be considered part of the inner surface of the cap. The other, second end of each sleeve 5 is present outside the cap and is open.

The cap 2 is essentially—i.e. apart from the projections 4f, 4g, 4n and indentations 4h, 4i and holes 3c, 4p—rotationally symmetrical with respect to the straight cap axis 6. The inner surface 4b of the inner shell 4 defines an osculating surface rotationally symmetrical with respect to the cap axis 6. Said osculating surface has a cylindrical section which fits closely on the free ends of the projections 4f, 4g and a section which fits closely on the free ends of the projections 4n and is curved in axial section. The three stems consisting of a sleeve 5 and the straight stem or sleeve axes 7 are, for example, uniformly distributed around the cap axis 6. The jacket 5a of each sleeve 5 is essentially—i.e. apart from the perforation—cylindrical and rotationally symmetrical with respect to the sleeve axis 7. The two shells 3, 4 have flat edges which are at right angles to the cap axis 6 and, when the prosthesis is assembled, are at least approximately flush with one another and together form the edge 2a of the entire cap.

The outer shell 3 consists of an outer material, namely of the alloy mentioned in the introduction and having cobalt and chromium as main components. The inner shell 4 consists of an inner material, namely of pure titanium. The inner shell is provided on its inner surface with a rough, porous, sprayed-on coating which forms at least the sections 4c, 4d of the inner surface 4b, which sections have projections and indentations, and namely the entire inner surface 4b and—as described in the introduction—consists essentially of titanium. The sleeves 5 likewise consist of pure titanium. That part of the outer surface of the jacket 5a which is present outside the holes 3c, 4p, the entire inner surface of said jacket and the inner surface of the end wall 5c of each sleeve are likewise provided with a sprayed-on, porous coating consisting essentially of titanium. Those sections of the inner surface of the cap 2 which are formed by the end walls 5c of the sleeves 5 thus consist of the same material as the main part of the inner surface of the cap, which main part is formed by the inner shell 4. It should be noted that the peak-to-valley heights of the sprayed-on coatings are substantially smaller than the heights of the projections 4f, 4g, 4n or the depths of the indentations 4h, 4i, 4m and the diameters of the holes 5b. The radially measured heights of the projections 4f, 4g, 4n and the radially measured depths of the indentations 4h, 4i, 4n are preferably at least 0.5 mm, at most 3 mm and, for example, 1 mm to 2 mm. The diameter of the holes 5f is, for example, 2 mm to 5mm. The average peak-to-valley height of the sprayed-on coatings is preferably at least 0.005 mm, at most 0.1 mm and, for example, 0.01 mm to 0.05 mm.

In the production of a prosthesis 1, the two shells 3, 4 and the sleeves 5 can be produced separately. In order to form the projections and indentations of the inner surface 4b of the inner shell 4, an inner shell having a smooth, rotationally symmetrical inner surface fitting closely on the summit of the projections to be formed can first be produced and the indentations then formed by an electoerosion method. It is possible instead to cast an inner shell having projections and indentations and then merely to subject this to a material-raising aftertreatment. To apply coatings to the inner surface 4b of the inner shell 4 and to the sleeves 5, a noble gas can be blown in a known manner through an electric arc and titanium hydride powder can be fed to the plasma jet produced. Said powder is decomposed in the plasma jet to give fine titanium droplets which are sprayed onto the parts to be coated.

If the shells 3, 4 and the sleeves 5 are separated from one another and have the same temperatures, the diameter of the cylindrical section of the outer surface 4a of the inner shell 4 may be, for example, slightly larger than the diameter of the cylindrical section of the inner surface 3b of the outer shell 3 or at least the same as the last-mentioned diameter. The same applies to the external diameter of that section of the sleeves 5 which is intended for insertion into the holes 3c, 4p and the internal diameter of the holes 3c, 4p of the shells. The two shells 3, 4 and the sleeves 5 may then be connected to one another simultaneously or in succession by press-fit connections. By heating and/or cooling certain parts, it is possible to ensure that the outer shell 3 has a higher temperature than the inner shell 4 when the shells are pressed one into the other and that the sleeves 5, when pressed into the holes 3c, 4p, have a lower temperature than the shells. When the shells and sleeves are once again at the same temperatures after being pressed one into the other, they fit very firmly one into the other.

FIG. 2 also shows a bone 9, namely a femur of a human adult. The bone 9 has an elongated shaft 9a which is shown only in part and is connected at its upper end via a neck 9b to a head 9c. The neck 9b projects away on one side of the bone shaft 9 and is inclined relative to the longitudinal direction of said shaft. Some blood vessels 10 serving for blood supply to the bone 9 are also shown in FIG. 2.

In order to attach the universal joint prosthesis 1 to and in the bone 9, its head 9c is exposed in a surgical operation, a guide wire is inserted into the head 9c and a layer of time head 9c is cut away with a profile cutter so that the bone stump or bone peg shown in FIG. 2 is formed. Its cut outer surface is rotationally symmetrical with respect to an axis which subsequently coincides with the cap axis 6 when the prosthesis 1 is mounted. That part of the bone which is bounded by the cut outer surface is furthermore approximately complementary to the inner space of the cap 2. The bone stump has a cylindrical outer surface whose diameter is preferably greater than the diameter of the cylindrical osculating surface fitting closely on the summit of the projections 4f, 4g of the cap 2 and smaller than the diameter of the cylindrical envelope surface surrounding the deepest points of the indentation 4h, 4i, 4m. After cutting the outer surface of the bone 9, annular holes—i.e. annular grooves which are very deep in comparison with their width—are cut into the bone with a hollow end-milling cutter and with the aid of a drilling template. These annular holes or grooves have dimensions such that the sleeves 5 have a tight fit therein. After this processing of the bone, the prosthesis 1 is mounted on the bone stump so that the cap 2 rests on the outer surface of the bone stump and the sleeves 5 project into the annular holes or grooves of the bone stump. When the cap 2 is mounted on the bone stump, parts of the projections 4f, 4g of the cap penetrate into the bone and profile the latter, as is shown in FIG. 3. Because of this and owing to the sleeves 5 fitting tightly into the annular holes or grooves in the bone, the prosthesis fits fairly firmly on and in the bone immediately after the operation without being attached with bone cement or another binder.

Large parts of the neck 9b and head 9c of the natural bone 9 and also many blood vessels through which blood is passed into the bone and out of the bone are retained in the operation. The axial dimension of that section of each sleeve 5 which is present outside the cap 2 is about 20% to 50% of the sphere diameter of the sphere defined by the outer surface 3a. Since the sleeves 5 therefore extend only approximately as far as the thinnest part of the neck 9b of the bone 9 and therefore do not project into its shaft 9a, this and all blood vessels present therein, some of which are relatively large, are retained. The retention of many blood vessels is advantageous for the healing of the bone and the formation of new bone material.

After a certain healing period, the bone stump formed by cutting during the operation, together with the subsequently grown bone material, fills the entire free part of the inner space of the cap 2 and of the sleeves 5 and in particular all indentations 4h, 4i, 4m present in the inner surface 4b of the cap and holes 5b in the sleeves 5. During healing, the bone also grows to the inner surface 4b of the inner shell 4 and to the various surfaces of the sleeves 5 and into the pores of these surfaces, so that it adheres firmly to these surfaces.

The inner surface 4b of the cap, which surface adheres to the bone 9, is substantially enlarged through its projections 4f, 4g, 4n and indentations 4h, 4i, 4m and through its porous nature in comparison with a smooth, pore-free reference osculating surface which is rotationally symmetrical with respect to the cap axis 6, has no projections and indentations and fits closely against the inner surface 4b. In addition, the sleeves 5, too, have large porous surfaces to which the bone adheres. This large embodiment of the surface of the prosthesis helps considerably to achieve a firm and permanent connection between the prosthesis and the bone.

If a person with the inserted prosthesis 1 stands on his legs and/or moves thereon, the person's body weight and any movements made by the person give rise to loads on the joint formed by the prosthesis 2 and an artificial or natural socket which is not shown. The result is, in particular, transverse forces or force components, i.e. lying in a plane at right angles to the cap axis 6, which forces or force components attempt to pull the cap 2 and the bone stump apart at certain points on the inner surface 4b of the cap 2. If the socket which is not shown exerts, for example, an approximately vertically downward force on the cap 2, a transverse force or force component which is directed away from the bone 9 and which is indicated by an arrow in FIG. 4 and denoted by $F_t$ is applied at the lower side of the cap 2. This transverse force or force component $F_t$ then produces forces $F_H$ which press the projections 4f, 4g against the bone sections present in the undercuts 4k. The undercuts 4k therefore help to ensure that the transverse forces or force components do not detach the bone adhering and growing at the inner surface 4b of the cap from the inner surface 4b. The indentations 4m between the projections 4f or 4g and 4n following in succession along the cap axis 6 help in particular to achieve good transmission of axial forces or force components, i.e. those parallel to the cap axis 6, from the cap 2 to the bone 9 and in the opposite direction. Furthermore, all projections 4f, 4g, 4n of the inner surface 4b prevent the cap from rotating about the cap axis 6 relative to the bone 9. The sleeves 5 distributed around the cap axis 6, together with their holes 5b through which the bone has grown, do of course help to transmit both transverse and axial forces from the prosthesis 1 to the bone 9 and in the opposite direction and help in particular to prevent rotations of the prosthesis relative to the bone about the cap axis 6. The prosthesis 1 therefore remains firmly bound to the bone 9 even under loads due to strong forces and forces rapidly changing in their magnitude and/or directions as well as torques.

A natural head of a femur defines an axis relative to which it is more or less rotationally symmetrical (at least in the healthy state). The neck of the femur is frequently not exactly rotationally symmetrical with respect to this axis. The surgeon can then determine the rotational point of the prosthesis relative to the cap axis 6 by virtue of the fact that the sleeves have sufficient space in the neck of the femur.

Figures 5, 6:
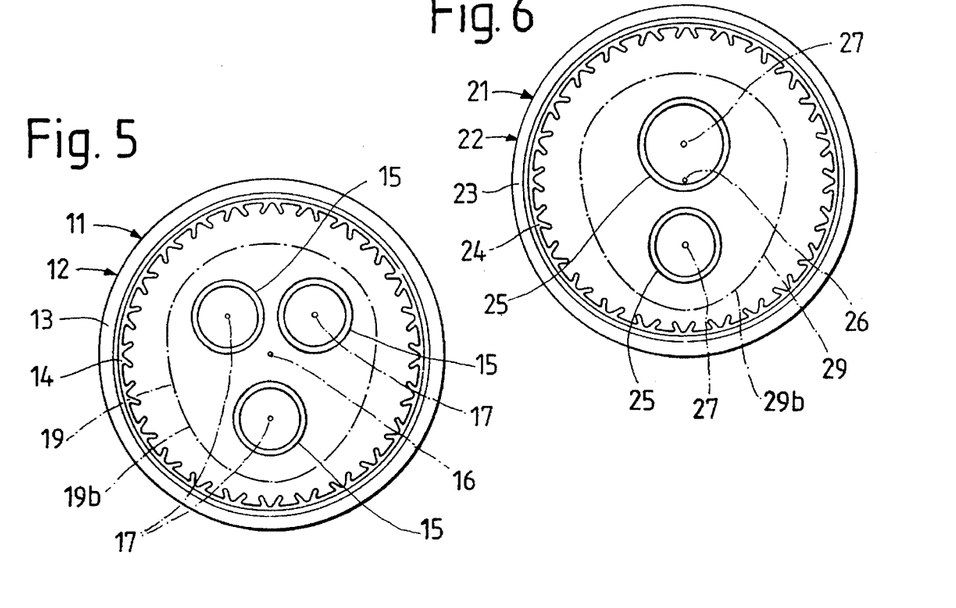
FIG. 5 is a simplified view of the open side of the cap of another prosthesis with three sleeves arranged nonuniformly around the cap axis.
FIG. 6 is a view, analogous to FIG. 5, of a prosthesis having two sleeves.

FIG. 5 shows a universal joint prosthesis 11 which is intended for attachment to a bone 19, namely to a femur, having a relatively highly asymmetrical neck 19b. The prosthesis 11 has a cap 12 with an outer shell 13 and an inner shell 14 and three sleeves 15. The cap 12 defines a cap axis 16. The sleeves 15 each define a sleeve axis 17. The prosthesis 11 is in general similar to the prosthesis 1 but differs from the latter in that the sleeves 15 and sleeve axes 17 are distributed nonuniformly about the cap axis 16 and may also be different distances away therefrom. This makes it possible to attach the prosthesis 1 on and in the bone 9 in such a way that those parts of all sleeves 19 which project into the neck 19b are enclosed, in cross-section, by a sufficiently thick layer of bone material.

The universal joint prosthesis 21 shown in FIG. 6 has a cap 22 which possesses an outer shell 23 and an inner shell 24, defines a cap axis 26 and is similar to the cap 12. The prosthesis 21 differs from the prosthesis 1 in that it has only two sleeves 25. These define sleeve axes 27 which are located, for example, in a common plane with the cap axis 26 present between them and may be different distances from the cap axis and may have different external diameters. The sleeves then have sufficient space in the highly asymmetric neck 29b of a bone 29, which neck is shown in FIG. 8.

Figure 7:
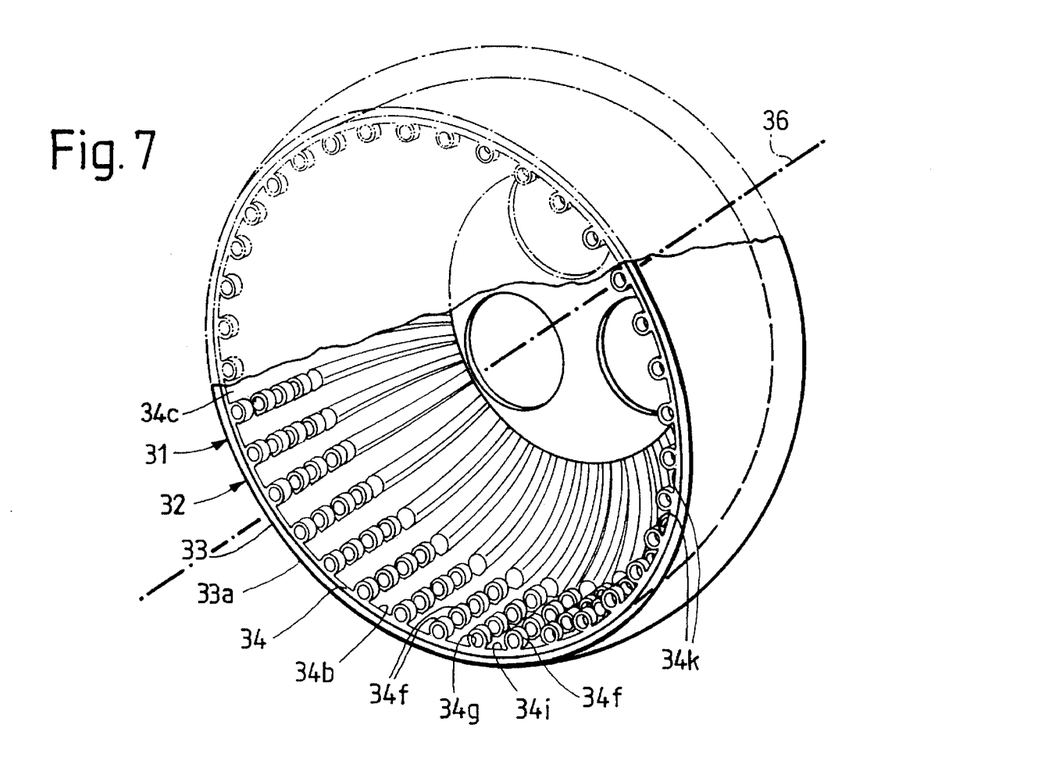
FIG. 7 is a perspective view of the cap of a prosthesis with an inner surface having annular projections.
Figure 8:
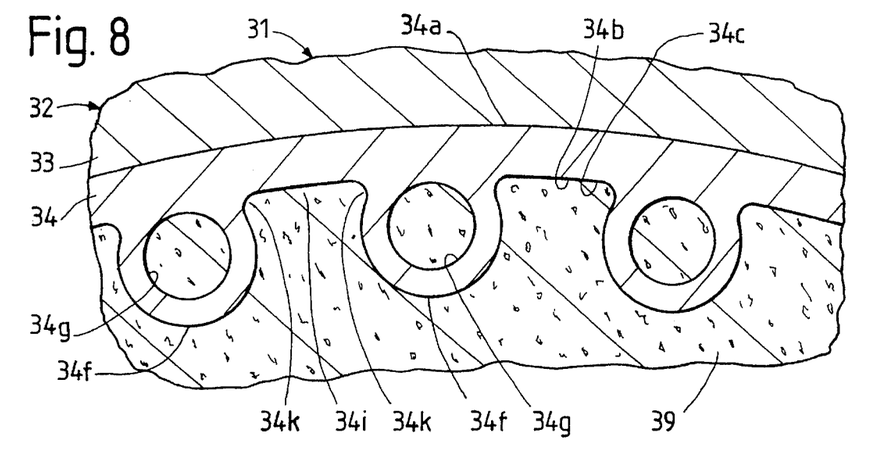
FIG. 8 is a cross-section through a region of the cap according to FIG. 7 after the bone has intergrown with the cap.

FIGS. 7 and 8 show part of the cap 32 of a universal joint prosthesis 31. The cap 32 has an outer shell 33 and an inner shell 34. The outer shell 33 has a calotte-shaped outer surface 33a. The inner shell 34 has an inner surface 34b. This has a jacket section 34c with a cylindrical osculating surface. The jacket section 34c has rows of projections 34f which are distributed along its circumference and are parallel to the cap axis 3b. Each projection 34f is approximately annular and/or C-shaped in a viewing direction parallel to the cap axis and has a through hole 34g, namely a bore. Each hole 34g has and/or defines a hole axis which lies in a plane passing through the cap axis and is in fact parallel to the cap axis 3b. The hole axis of each hole 34g accordingly forms an at least approximate right angle with a normal to that section of the outer surface 33a which is adjacent to the relevant hole and also with a normal to the section, adjacent to the relevant hole, of a cylindrical osculating surface which is rotationally symmetrical with respect to the cap axis 3b and fits closely on the summit of the projections 34f. This osculating surface is a surface which is defined by the summits or tips of each of the plurality of projections. An indentation 34i is present between the pairs of projections 34f following in succession along the circumference of the cap. Each indentation 34i has a small undercut 34k in that side of its base which is adjacent to a projection 34f, so that the base section of each indentation 34i is therefore more or less swallowtail-shaped in cross-section.

Unless stated otherwise above, the prosthesis 31 may be formed similarly to one of the prostheses 1, 11, 21 and in particular may have sleeves with a perforated jacket.

If a prosthesis 31 is attached to a bone denoted by 39 in FIG. 8, namely a femur, the bone 39 may engage the undercuts 34k during its healing and in particular may grow through the holes 34g. The bone sections engaging the undercuts 34k and penetrating through the holes 34g effectively prevent the bone 39 from becoming detached from the inner surface 34b of the cap 32 even under strong transverse forces and/or transverse forces which rapidly change their magnitude and direction. Otherwise, the prosthesis 31 has properties similar to those of the prosthesis 1.

Figure 9:
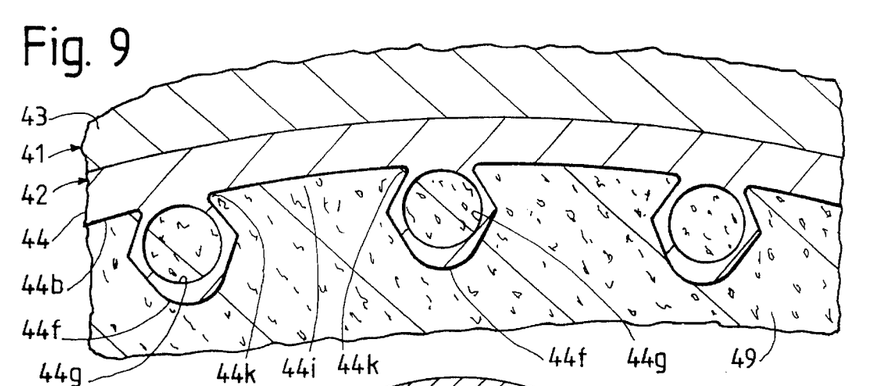
FIG. 9 is a section, corresponding to FIG. 8, of the cap of a prosthesis with other annular projections.

The universal joint prosthesis 41 shown in part in FIG. 9 once again has a cap 42 with an outer shell 43 and an inner shell 44. The inner surface 44b of the inner shell once again has a section with a cylindrical osculating surface which, as in the case of the prosthesis 31, is provided with annular projections 44f having a hole 44g. An indentation 44i is present between each pair of projections adjacent in cross-section. Each projection 44f has, in its region abutting the base of an indentation 44i, flat outer surface sections which, in cross-section and toward the interior of the cap, are inclined relatively sharply away from one another. That section of an indentation 44i which abuts the base of said indentation is therefore swallowtail-shaped in cross-section and has two pronounced undercuts 44k which a bone 49 can engage.

Figure 10:
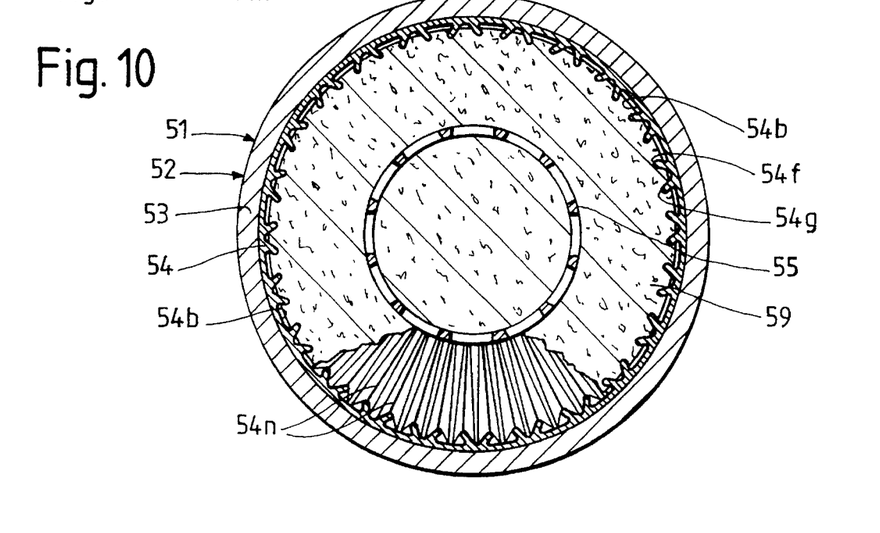
FIG. 10 is a cross-section, analogous to FIG. 3, through a prosthesis having only a single sleeve.

The universal joint prosthesis 51 according to FIG. 10 has a cap 52 with an outer shell 53 and an inner shell 54. Its inner surface 54b has, for example, projections 54f, 54g and 54n, which are approximately the same as the projections 4f and 4g and 4n, respectively, of the prosthesis 1. However, the prosthesis 51 has only a single sleeve 55 which is arranged coaxially with the cap axis and has a perforated jacket. The sleeve can be attached to a bone 49 which is shown in FIG. 10—analogously to the bone 9 in FIG. 3—in the condition immediately after he operation.

Figure 11:
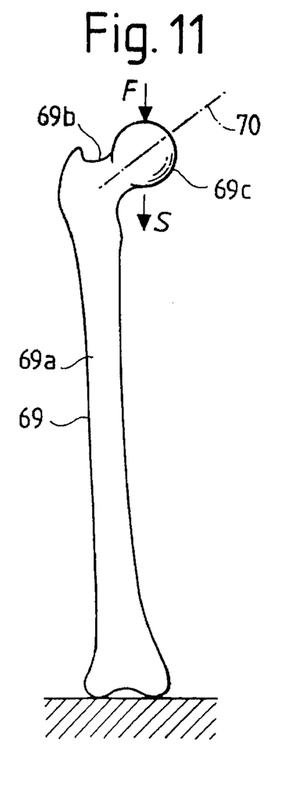
FIG. 11 is a schematic view of an arrangement of a femur having a natural head for measurement of the deflection of the latter.
Figure 12:
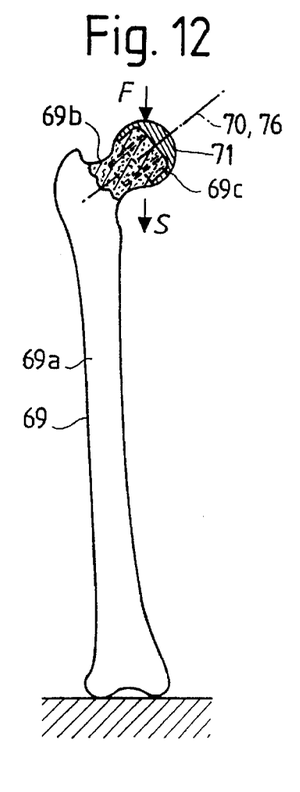
FIG. 12 is a view, analogous to FIG. 11, of the femur after the latter was provided with a prosthesis according to the invention, having a cap and a sleeve.
Figure 13:
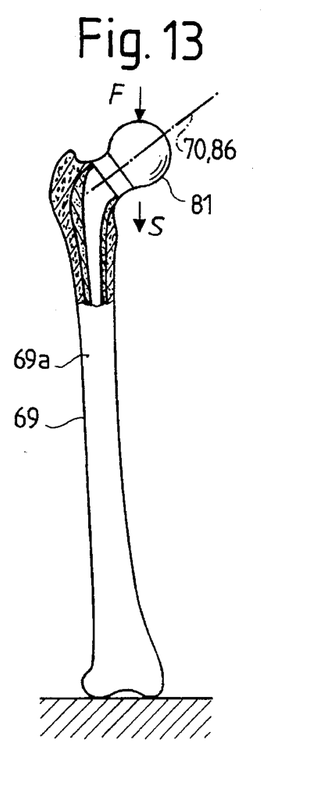
FIG. 13 is a view, analogous to FIGS. 11 and 12, of the femur shown in these Figures after said femur was provided with a prosthesis which is not according to the invention and has a solid head and a bent or curved shaft.

FIGS. 11, 12 and 13 show a bone 69, namely a human femur, which was removed from a cadaver of an adult male for investigating its deformation due to loads. In FIG. 11, the bone 69 is in its natural state, in which it has a shaft 69a, a neck 69b and a natural, unchanged head 69c. The head 69c defines an axis 70 which passes through it and through the neck 69b and relative to which the head is more or less exactly rotationally symmetrical and which makes an angle of, for example, about 120° to 130° with the shaft 69b or—more precisely—with its longitudinal direction or longitudinal axis. For investigating the deformation, the bone 69 was arranged approximately in the position which it assumes in an erect person. The bone was supported at its lower end and was fixed and the head 69c was subjected to a force F directed vertically downward. The latter is accordingly more or less parallel to the shaft 69a and makes an angle of about 45° to 60° with axis 70. The bone 69 is elastically deformed and in particular curved by the force F, the head being swivelled downward. Inter alia, the deflection S of the head 69c parallel to the force F was measured in the investigations. The deflection S of the natural head 69c as a function of the force F is represented by the curve 91 in the graph shown in FIG. 14.

After the investigation of the natural bone 69, the latter was processed in such a way that the universal joint prosthesis 71 according to the invention which is shown in FIG. 12 could be mounted on the bone. The prosthesis 71 used for the deformation test had a cap and only a single sleeve attached thereto and was thus essentially the same as the prosthesis 51 shown in FIG. 10. After mounting of the prosthesis 71, its cap axis 76 coincided at least approximately with the axis 70 of the head 69c. Since the bone 69 taken from a cadaver could not of course intergrow with the prosthesis through formation of new bone material, the formation of new bone material was simulated by applying a binder which more or less filled the indentations in the inner surface of the cap and the holes in the sleeve. The deflection S resulting in the case of such an attachment of the prosthesis 71 according to the invention is represented by the curve 92 in FIG. 14.

After the investigation of the bone 69 provided with the prosthesis 71, the head 69c and neck 69b of said bone was cut off from the shaft 69a and the latter was provided with a hole. The universal joint prosthesis 81 which is not according to the invention and is shown in FIG. 13 was then attached in the bone 69. The prosthesis 81 has the form already described in the introduction and has a solid head and an angled or curved shaft or stem, which was cemented in the shaft 69a of the bone 69. The deflection S resulting on application of a force F to the head of the prosthesis 81 is represented by the curve 93 in FIG. 14.

Figure 14:
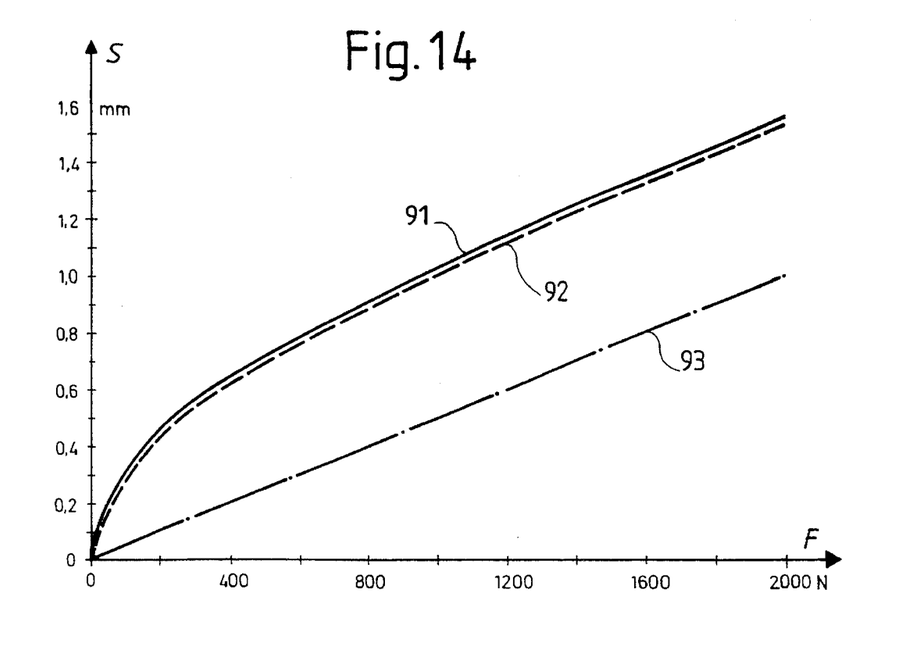
FIG. 14 is a graph in which the deflection of the heads shown in FIGS. 11 and 13 is plotted as a function of a force acting on said heads.

In the various deformation investigations, the deflection S was measured for forces F with values from 0 to 2000N. In this force range, the bone 69 undergoes essentially elastic deformation. The deflections measured for the completely natural bone 94 and for the bone with the prosthesis 71 according to the invention are, according to the curves 91 and 92, virtually identical under the same force in the entire force range investigated. According to the curves 91 and 92, the deflection initially increases relatively steeply from zero point in the case of the completely natural bone and in the case of the bone provided with a prosthesis 71 according to the invention. The slopes of the two curves 91, 92 and the associated differential coefficients dS/dF of the deflection S with respect to the force F initially decrease approximately steadily with a force increasing from zero. When the force F exceeds a value of about 400N or 500N, the slopes of the curves 91, 92 and the differential coefficients then remain virtually constant up to a force of 2000N. In both curves 91, 92, the differential coefficient dS/dF is substantially smaller for forces between 500N and 1000N than for forces between 0 and 100N and, in the case of forces between 500N and 1000N, is at most 70% and namely even only at most 50% of the differential coefficients obtained in the case of forces up to at most 100N.

If, on the other hand, the bone 69 is provided with the prosthesis 81 not according to the invention, the curve 93 indicates that the deflection S changes approximately linearly with force in the entire investigated range, so that the differential coefficient dS/dF is practically constant from 0 to 2000N. Furthermore, a substantially smaller deflection than in the case of a completely natural bone and in the case of a bone having a prosthesis according to the invention is then obtained in the entire force range. The deformation properties and the bending strength of a bone are thus changed by the prosthesis 71 according to the invention to a much lesser extent than by a prosthesis 81 not according to the invention.

If, in an exceptional case—for example owing to pathological damage to the head and neck of the bone or owing to an error during the operation or for another reason—a prosthesis according to the invention does not hold sufficiently firmly in the bone, it is still possible to cut off the entire head and neck of the bone and to attach a prosthesis 81 according to the invention to the remaining part of the bone. If a prosthesis 81 not according to the invention is used first and then fails to hold, attaching another prosthesis to the bone is then often difficult and is possible only with a loss of still more natural bone material.

The prostheses according to the invention can also be modified in other ways. In particular, features of the different prostheses shown in FIGS. 1 to 10 can be combined with one another and furthermore, for example, only one sleeve may be provided in a prosthesis having annular projections 34f or 44f.

Furthermore, the inner surface of the cap may have a section with projections which in general is slightly conical and widens toward the edge of the cap, instead of a generally cylindrical section or in addition to such a section. The summit of said projections may then define a conical osculating surface. If the projections are annular, the axes of their holes can then be formed by lines of intersection of planes passing through the cap axis with a conical surface.

It is also possible to fill the V-shaped indentations 4h with material of the inner shell of the cap so that each pair of adjacent projections 4f, 4g inclined away from one another toward their free ends is replaced by a single projection. This projection has then two opposed lateral surfaces that are inclined away from each other toward the free end of the projection and toward the central region of the free interior of the cap. This projection is then undercut at both lateral surfaces and swallowtail-shaped or dovetailed in cross-section. Adjacent projections limit then pairwise indentations that are swallowtail-shaped or dovetailed in cross-section and that have for instance similar shapes as the indentations 4i.

The inclined projections 4f, 4g can also be replaced by tab-shaped projections each having two opposed, lateral surfaces that are substantially plane and parallel to each other and to a middle plane that is parallel to the cap axis 6 and extends through the cap axis. These projections can be distributed regularly around the axis. The middle planes of two adjacent projections are then approaching each other toward free interior of the cap and towards the cap axis. The lateral surfaces that belong to two adjacent projections and face each other are then also slightly approaching each other toward the free, inner ends of the projections and toward the central region of the free interior of the cap in cross-section. The indentation disposed between these two lateral surfaces is slightly narrowing away from the base of the indentation towards the open end of the indentation and towards the cap axis. The indentation is, thus, slightly swallowtail-shaped or dovetailed in cross-section. One may also say that projections of this kind have slight undercuts or accomplish at least a similar object as undercuts due to the geometry of the cap.

Furthermore, the other surfaces of the jackets of the sleeve may also be provided with projections and/or indentations distributed along the circumference of the sleeves and along the sleeve axis.

Instead of forming at least parts of the inner surface of the cap and of the surfaces of the sleeve(s) by a layer of sprayed-on titanium, one may make the inner surface of the cap and the surfaces of the sleeve(s) by other methods at least partly rough and/or porous. One might for instance apply other porous coatings or making said surfaces rough and/or porous by chemical etching, electroerosion, shot-peening or other chemical, electrochemical or mechanical surface treatments.

What is claimed is:

1. A universal joint prosthesis comprising:

a hollow cup shaped cap, said cap having an outer surface and an inner surface, said inner surface being configured for attachment to a bone, said cap having a cap axis;

a plurality of projections positioned along a circumference of said inner surface, each of said projections being inclined away from a radial direction of said inner surface and towards said inner surface over substantially an entire length of each of said projections, each of said projections defining an undercut between each of said projections and said inner surface, each of said projections having substantially flat first and second surfaces positioned on substantially opposite sides of a cross section of each of said projections, said cross section being perpendicular to said cap axis, said first surface being connected to said inner surface by a continuously curved base transition surface, said first and second surfaces of each of said projections being connected to each other at a free end of each of said projections by a continuously curved free end transition surface.

2. A universal joint prosthesis in accordance with claim 1, wherein:

said plurality of projections define an osculating surface including summits of said plurality of projections, osculating surface having one of a cylindrical and conical section.

3. A universal joint prosthesis in accordance with claim 1, wherein:

adjacent pairs of said projections are inclined toward each other and define a cross-sectional indention defining an acute angled dado profile.

4. A universal joint prosthesis in accordance with claim 1, wherein:

said first and second flat surfaces of each of said projections are substantially parallel to each other;

said plurality of projections are aligned along said circumference of said inner surface and are inclined alternately towards and away from each other.

5. A universal joint prosthesis in accordance with claim 4, wherein:

said outer surface forms a part of a spherical surface;

said inner surface has a substantially cylindrical section;

said plurality of projections are aligned in rows which are substantially straight and substantially parallel to said cap axis;

said first surface of each of said projections is adjacent a respective undercut of a respective projection and connects with said cylindrical section of said inner surface;

said second surface of each of said projections being connected with a second surface of an adjacent said projection by a continuously curved transition surface.

6. A universal joint prosthesis in accordance with claim 1, further comprising:

a stem having an end rigidly connected to said cap and extending from said cap into an inner space defined by said inner surface, said stem being substantially straight and having an axis substantially parallel to said cap axis.

7. A universal joint prosthesis in accordance with claim 6, further comprising:

another stem having an end rigidly connected to said cap and extending from said cap into said inner space defined by said inner surface, said another stem being substantially straight and having an axis substantially parallel to said cap axis.

8. A universal joint prosthesis in accordance with claim 6, wherein:

said stem is formed as a sleeve and has another end projecting out of said inner space, said another end being opened, said sleeve defining perforations.

9. A universal joint prosthesis in accordance with claim 6, wherein:

said outer surface is formed as a section of a spherical surface, said spherical surface having a sphere diameter, said stem having a section extending out of said inner space, said section of said stem having a length parallel to said cap axis, said length of said section being between 10% and 100% of said sphere diameter.

10. A universal joint prosthesis in accordance with claim 6, wherein:

said cap and said stem are formed of materials and are shaped to be configure for attachment to a bone stump extending radially outward from a shaft of a human femur so that when a force between 500N and 1000N is applied to said cap parallel to said shaft a differential coefficient of cap deflection parallel to said shaft is at most 70% of a differential coefficient of cap deflection at a force of substantially 100N.

11. A universal joint prosthesis in accordance with claim 10, wherein:

said cap and said stem are formed of materials and are shaped to cause said differential coefficient to initially decrease steadily from an initial value to a substantially constant value as said force increases, in a manner substantially similar to a differential coefficient of deflection of a head of a human femur with a natural head.

12. A universal joint prosthesis in accordance with claim 1, wherein:

said outer surface is formed of an outer material and said inner surface is formed of an inner material, said outer and inner materials having a different chemical composition, said outer material has a smaller coefficient of sliding friction than said inner material and said inner material causes a firmer bond with a bone than said outer material for an identical surface characteristic.

13. A universal joint prosthesis comprising:

a hollow cup shaped cap, said cap having an outer surface and an inner surface, said inner surface being configured for attachment to a bone, said outer surface forming a section of a spherical surface and said cap having a cap axis;

a plurality of projections positioned along a circumference of said inner surface, pairs of adjacent projections being arranged to define an indentation between each said pair of projections, said indentations defining a substantially acute angled dado profile in a cross-section perpendicular to said cap axis, a subset of said plurality of projections each define a through hole, each through hole having a hole axis line in a plane which passes through said cap axis;

first and second stems having an end rigidly connected to said cap and extending from said cap into an inner space defined by said inner surface, said first and second stems being substantially straight and having an axis substantially parallel to said cap axis, said first and second stems being each formed as a sleeve and each sleeve having another end projecting out of said inner space, said each another end being opened, said each sleeve defining perforations.

14. A universal joint prosthesis in accordance with claim 13, wherein:

said stem has a section extending out of said inner space, said section of said stem having a length parallel to said cap axis, said length of said section being between 10% and 100% of said sphere diameter.

15. A universal joint prosthesis in accordance with claim 13, wherein:

said hole axis of said projection are substantially parallel to said cap axis.

16. A universal joint prosthesis comprising:

a hollow cup shaped cap having an outer surface and an inner surface, said inner surface being configured for attachment to a bone, said outer surface forming a section of a spherical surface and said cap having a cap axis, said outer surface is formed of an outer material and said inner surface is formed in a major part of an inner material, said outer material includes one of ceramic and an alloy having cobalt as a main component, said inner material includes one of titanium, a titanium alloy and a mixture of tantalum and zirconium;

a plurality of projections positioned along a circumference of said inner surface, said plurality of projections are shaped to include an undercut in a cross-section perpendicular to said cap axis, said plurality of projections being formed of said inner material;

a stem having an end rigidly connected to said cap and extending from said cap into an inner space defined by said inner surface, said stem being substantially straight and having an axis substantially parallel to said cap axis, said stem being formed as a sleeve and has another end projecting out of said inner space, said another end being opened, said sleeve defining perforations, said stem being formed of said inner material.

17. A universal joint prosthesis in accordance with claim 16, wherein:

said outer material forms an outer shell;

said inner material forms an inner shell, said inner shell is connected to said outer shell by one of a press-fit connection and a weld connection.

18. A universal joint prosthesis comprising:

a hollow cup shaped cap, said cap having an outer surface and an inner surface, said inner surface being configured for attachment to a bone, said cap having a cap axis;

a plurality of projections positioned along a circumference of said inner surface, said plurality of projections being arranged on said inner surface in a plurality of rows, each of said plurality of rows being located in planes substantially parallel to said cap axis, each of said projections defining a hole and two undercuts, said hole of each of said projections having a hole axis substantially parallel to said cap axis, said two undercuts being positioned on opposite sides of said projection in a plane passing through said cap axis and said hole axis of a respective projection.

19. A universal joint prosthesis in accordance with claim 1, wherein:

said projections form means for penetrating into a bone stump when said cap is inserted onto the bone stump;

said each projection is spaced and separate from other said projections.

* * * * *